United States Patent [19]

Itagaki et al.

[11] Patent Number: 4,780,152
[45] Date of Patent: Oct. 25, 1988

[54] KIT FOR CONTACT LENS CLEANING AND METHOD FOR CONTACT LENS CLEANING

[75] Inventors: Yoko Itagaki, Saitama; Masahiro Hiranuma, Honjo, both of Japan

[73] Assignee: Hoya Corporation, Tokyo, Japan

[21] Appl. No.: 73,998

[22] Filed: Jul. 16, 1987

[30] Foreign Application Priority Data

Aug. 15, 1986 [JP] Japan ................................ 61-191520

[51] Int. Cl.⁴ ............................................... A61K 9/08
[52] U.S. Cl. ........................................ 134/42; 134/26; 252/95; 252/105; 252/106; 252/90; 252/174.13; 422/37
[58] Field of Search ...................... 134/42, 26; 252/95, 252/105, 106, 90, 174.12, 174.13, 174.17; 422/37

[56] References Cited

U.S. PATENT DOCUMENTS

| | | | |
|---|---|---|---|
| 4,552,679 | 11/1985 | Schobel et al. | 252/90 |
| 4,642,234 | 2/1987 | Davies et al. | 252/106 |
| 4,670,178 | 6/1987 | Huth et al. | 252/95 |
| 4,690,772 | 9/1987 | Tell et al. | 252/106 |

FOREIGN PATENT DOCUMENTS

| | | |
|---|---|---|
| 7703474 | 7/1976 | Australia . |
| 2722784 | 10/1984 | Australia . |
| 0139994 | 5/1985 | European Pat. Off. . |
| 0147100 | 7/1985 | European Pat. Off. . |
| 0175801 | 4/1986 | European Pat. Off. . |
| 2256767 | 8/1975 | France . |
| 2544880 | 10/1984 | France . |
| 0018617 | 2/1983 | Japan ................................ 252/106 |
| 2003033 | 3/1979 | United Kingdom ................ 252/106 |

*Primary Examiner*—Asok Pal
*Attorney, Agent, or Firm*—Bert J. Lewen; Henry Sternberg

[57] ABSTRACT

Contact lenses can be cleaned effectively in a short time, by using a kit for contact lens cleaning which comprises an oxidizing agent for removing stains adhering to contact lenses and a reducing agent for making nontoxic the oxidizing agent still remaining after stain removal and wherein the oxidizing agent and the reducing agent are each in such a form that when they are placed in water substantially simultaneously, the major portion of the oxidizing agent dissolves in the water more rapidly than the major portion of the reducing agent. Further, with this kit, the cleaned contact lenses can be made nontoxic without fail.

10 Claims, No Drawings

KIT FOR CONTACT LENS CLEANING AND METHOD FOR CONTACT LENS CLEANING

BACKGROUND OF THE INVENTION

1. Field of the Invention

The present invention relates to a kit for contact lens cleaning, as well as to a method for contact lens cleaning. The present invention is applied to cleaning of known contact lenses composed mainly of, for example, methyl methacrylate, silicone-containing methacrylate, hydroxyethyl methacrylate, butyl acrylate or the like.

2. Description of the Related Art

Methods for cleaning contact lenses to remove stains adhering thereto are already known and various compositions have been proposed for this purpose.

For example, Japanese Patent Application Kokai (Laid-Open) No. 42614/1982 discloses a method wherein a contact lens is immersed in an aqueous solution containing, for example, a hypochlorite, a chlorinated lime and chloramine to clean the lens. This method has a sufficient cleaning effect but pays no attention for making the cleaned lens safe by, for example, applying to the cleaned lens a treatment for making it nontoxic. Japanese Patent Application Kokai (Laid-Open) No. 119113/1981 discloses a method wherein a contact lens is immersed in an aqueous solution containing a hypohalogenite for a necessary length of time to remove stains adhering to the lens. In this method, a reducing agent is dissolved in the cleaning solution, after the immersion treatment for a necessary length of time, to make the solution nontoxic and, when the reducing agent is a saccharide such as glucose, mannose or the like, it can be dissolved in the cleaning solution prior to the immersion. These methods, however, are defective in that the treatment for making the solution nontoxic may be forgotten and the visual check of the completion timing of such a treatment is difficult.

Thus, the conventional methods for removing stains from contact lenses have a sufficient stainremoving effect but have drawbacks, for example, in that the safety of cleaned lens is low, that the cleaning operation becomes lengthy because two cleaning components are added separately, that the addition of one cleaning component is forgotten resulting in the reduced safety of cleaned lens, and that the safety of cleaned lens can not be ascertained.

SUMMARY OF THE INVENTION

An object of the present invention is to provide a novel kit for contact lens cleaning which can remove stains adhering to contact lenses, effectively in a short time, which can reliably conduct, after stain removal, a treatment for making the cleaned lenses nontoxic, and which can easily and visually check the completion timing of said treatment for making the cleaned lenses nontoxic, as well as a method for contact lens cleaning using said kit.

Another object of the present invention is to provide a kit for contact lens cleaning which can conduct both stain removal and a treatment for making the cleaned lens nontoxic only in a single cleaning operation and makes completely safe the possible wearing of the resulting lens right after the operation without washing the lens with tap water, purified water or running water, as well as a method for contact lens cleaning using said kit.

Still another object of the present invention is to provide a kit for contact lens cleaning which gives no adverse effect on the shape, color tone, etc. of contact lens even when the lens is subjected to repeated cleaning with the kit and accordingly which can conduct the cleaning of contact lens safely and reliably, as well as a method for contact lens cleaning using said kit.

These objects of the present invention can be achieved by the following kit and method for contact lens cleaning.

According to the present invention, there are provided a kit for contact lens cleaning, comprising an oxidizing agent for removing stains adhering to contact lenses and a reducing agent for making nontoxic the oxidizing agent still remaining after stain removal, wherein the oxidizing agent and the reducing agent are each in such a form that the oxidizing agent and the reducing agent do not substantially react with each other in the kit and that when they are placed in water substantially simultaneously, the major portion of the oxidizing agent dissolves in the water more rapidly than the major portion of the reducing agent, and a method for contact lens cleaning by using an oxidizing agent for removing stains adhering to contact lenses and a reducing agent for making nontoxic the oxidizing agent still remaining after stain removal, the oxidizing agent and the reducing agent being each in such a form that when they are placed in water substantially simultaneously, the major portion of the oxidizing agent dissolves in the water more rapidly than the major portion of the reducing agent, the method comprising placing the oxidizing agent and the reducing agent in water substantially simultaneously to dissolve the major portion of the oxidizing agent more rapidly than the major portion of the reducing agent and immediately conducting a cleaning treatment of lens by the oxidizing agent and a treatment of the residual oxidizing agent by the reducing agent for making the residual oxidizing agent nontoxic, macroscopically in this order.

DESCRIPTION OF THE PREFERRED EMBODIMENT

The present invention will be explained specifically.

The oxidizing agent which is a first essential component in the kit for contact lens cleaning according to the present invention is to remove stains adhering to contact lenses. It is preferably compounds capable of releasing available chlorine, such as a chlorinated lime, chloramine T, chloramine B, halazone, calcium hypochlorite and the like. Of these, a chlorinated lime and chloramine T are especially preferable.

The reducing agent which is a second essential component in the kit for contact lens cleaning according to the present invention is to make nontoxic the oxidizing agent still remaining after stain removal. It is preferably hydroxycarboxylic acids and salts thereof, such as citric acid, malic acid, tartaric acid, ascorbic acid, and their sodium, potassium, calcium and other salts. Of these, citric acid, sodium citrate and ascorbic acid are especially preferable.

As the kit containing the oxidizing agent and the reducing agent, there can be mentioned a package. The package has no particular restriction as long as it is made of a material giving substantially no adverse effect on the oxidizing agent and the reducing agent. Typical examples of the package include a three sides-sealed aluminum package and stick-shaped aluminum package.

As the kit, there can also be mentioned a capsule containing the oxidizing agent and the reducing agent. Such a capsule has no restriction as long as it is water-soluble.

Each of the oxidizing agent and the reducing agent constituting the kit of the present invention must take a form satisfying both of the following requirements (I) and (II).

(I) The oxidizing agent and the reducing agent do not substantially react with each other in the kit, for example, package.

(II) When the kit, for example, a package is opened and each component is placed in water, the major portion of the oxidizing agent dissolves in the water more rapidly than the major portion of the reducing agent.

In the requirement (I), "do not substantially react with each other" implies that the oxidizing agent and the reducing agent do not at all or significantly react with each other while they are contained in the kit, for example, a package, so that they can achieve respective intended purposes (a cleaning treatment of lens in the case of the oxidizing agent and a treatment of the residual oxidizing agent for making it nontoxic in the case of the reducing agent) when the package is opened and each component is placed in water. Accordingly, even if a very small portion of the oxidizing agent and a very small portion of the reducing agent make mutual contact in, for example, a package to cause an extremely low level of reaction, it is no problem as long as the residual unreacted oxidizing agent and the residual unreacted reducing agent can achieve respective intended purposes when they are placed in water.

In the requirement (II), "the major portion of the oxidizing agent dissolves in water more rapidly than the major portion of the reducing agent" implies that when they are placed in water substantially simultaneously, the dissolution peak of the oxidizing agent appears earlier than the dissolution peak of the reducing agent. Accordingly, even if both the dissolution of the oxidizing agent and the dissolution of the reducing agent start simultaneously at a certain timing after they have been placed in water, it is no problem as long as macroscopically the cleaning treatment of contact lens by the oxidizing agent takes place first and the treatment of the residual oxidizing agent by the reducing agent for making the residual oxidizing agent nontoxic takes place next.

In order for the oxidizing agent and the reducing agent to satisfy the requirements (I) and (II), it is preferred that the oxidizing agent be in a form of powders or granules and the reducing agent be in a form of tablets. The reason is that the oxidizing agent and the reducing agent, when each is in said form as compared with when both of them are in a form of powders or granules, have a low degree of mutual contact and do not substantially react with each other and, when they are placed in water, the oxidizing agent in powder or granule form dissolves in the water more rapidly than the reducing agent in tablet form.

When the oxidizing agent is used in a form of powders or granules, it is possible to add a filler such as NaCl, KCl, lactose and/or dextrose or the like in order to make measuring easier.

When the reducing agent is used in a form of tablets, coating of the tablets with a coating agent is particularly preferable because it can completely prevent the direct reaction between the oxidizing agent and the reducing agent in the kit, for example, a package and moreover, when they are placed in water, the reducing agent can start dissolution, after the oxidizing agent has sufficiently achieved its purpose, to conduct a treatment of the residual oxidizing agent for making it nontoxic [whereby the simultaneous occurrence of (a) lens cleaning by the oxidizing agent and (b) a treatment of the residual oxidizing agent by the reducing agent can be minimized and the two components can be utilized efficiently].

As the coating agent, there are preferred, for example, carboxymethylethylcellulose, cellulose acetate phthalate, hydroxypropylmethylcellulose phthalate, a methacrylic acid-ethyl acrylate copolymer and a methacrylic acid-methyl acrylate copolymer. Any coating agent can be used as long as it is soluble in aqueous solutions having a pH of 5.5 or above.

Tablets containing the reducing agent are preferred to be effervescent tablets in order to reliably conduct a treatment of the residual oxidizing agent for making it nontoxic. The component added to make tablets effervescent include sodium bicarbonate, potassium bicarbonate, etc. Any of these components can achieve a purpose of foaming. The tablets may further contain a lubricant, a disintegrating agent, etc., ordinarily used in tablet preparation.

In order to satisfy the requirements (I) and (II), the oxidizing agent and the reducing agent can also be in such a form that both of them are in a form of powders or granules and, in order to avoid their mutual contact, the reducing agent is contained in a bag or coated with a coating agent. In this case as well, when the kit (e.g. a package) containing the oxidizing agent and the reducing agent is placed in water, the oxidizing agent dissolves in the water more rapidly than the reducing agent contained in a bag or coated with a coating agent, whereby the object of the present invention can be achieved.

The bag has no particular restriction as long as it is soluble in aqueous solutions having a pH of 5.5 or above. The coating agent used for coating the reducing agent of powder or granule form can be same as that used for coating the tablets.

The method for contact lens cleaning using the kit of the present invention will be described. The concentration of the oxidizing agent after dissolution in water is preferred to be 5.0 to 0.005% by w/v ordinarily. When the oxidizing agent is, for example, a bleaching powder which is a compound capable of releasing available chlorine, the concentration of the bleaching powder during the cleaning treatment is suitably 1.0 to 0.01% by w/v after dissolution in water. When the concentration is lower than 0.01% by w/v, the effect of the bleaching powder is small and a treatment of long time is required. When the concentration is higher than 1.0% by w/v, no corresponding increase in effect is obtained. A more preferable concentration of the bleaching powder is 0.5 to 0.1% by w/v after dissolution in water.

The concentration of the reducing agent during use must be such that it provides an amount sufficient for the reduction of the residual oxidizing agent and yet gives no effect on the pH and osmotic pressure of the solution after treatment. The concentration of the reducing agent after dissolution in water is preferred to be 10.0 to 0.05% by w/v ordinarily. When the reducing agent is, for example, citric acid or sodium citrate, their concentrations after dissolution in water are preferably 2.0 to 0.1% by w/v (citric acid) and 5.0 to 0.5% by w/v (sodium citrate), more preferably 1.0 to 0.2% by w/v (citric acid) and 3.0 to 1.0% by w/v (sodium citrate).

Based on these concentrations after dissolution in water, the amounts of the oxidizing agent and the reducing agent in a kit are determined.

According to the method for contact lens cleaning using the kit of the present invention, when the oxidizing agent and the reducing agent are placed in water substantially simultaneously, the major portion of the oxidizing agent dissolves in water more rapidly than the major portion of the reducing agent because the oxidizing agent and the reducing agent take the above mentioned forms. As a result, the oxidizing agent starts cleaning of contact lens; simultaneously, the reducing agent begins to dissolve in water slowly; and after the oxidizing agent has achieved its purpose of removing stains adhering to a contact lens, the reducing agent treats the residual oxidizing agent to make it nontoxic. This treatment of the residual oxidizing agent by the reducing agent to make the former nontoxic is complete when the reducing agent has dissolved completely. When the reducing agent is tablets, the timing of complete dissolution of the reducing agent can be confirmed definitely by visually checking the complete disappearance of the tablets. Therefore, a reducing agent in tablet form is preferred particularly.

In a preferred embodiment of the present invention wherein the reducing agent is coated tablets, firstly the oxidizing agent dissolves and starts cleaning of contact lens; simultaneosuly, the coating agent on tablets begins to dissolve slowly; in 5 to 30 minutes, the reducing agent present in tablets begins to dissolve slowly while foaming in the case of, for example, effervescent tablets and starts a reaction with the residual oxidizing agent to make it nontoxic. Thus, the cleaning treatment of lens by the oxidizing agent and the treatment of the residual oxidizing agent by the reducing agent for making the residual oxidizing agent nontoxic are conducted in different time spans and this is preferable particularly.

The cleaning method of the present invention can be applied to cleaning of all known contact lenses. It is desired, however, that the solution after treatment be isotonic with and have the same pH as the human lacrima in view of (a) the fact that in particular, hydrogel contact lenses composed mainly of hydroxyethyl methacrylate or the like may undergo shape change by the osmotic pressure, pH, etc. of treating solution used and (b) the compatibility of cleaned contact lens with eyes. For this purpose, it is possible to add to the oxidizing agent and the reducing agent, isotonicity such as NaCl, KCl, glucose and the like and buffer agents such as boric acid sodium borate, sodium hydrogenphosphate, sodium acetate, sodium carbonate and the like, all employed ordinarily. The before-mentioned hydroxycarboxylic acid or salt thereof and foaming agent may be also used as pH-adjusting agent.

The kit of the present invention is used in the following manner periodically, for example, weekly, biweekly or monthly. That is, a contact lens is removed from eyes, washed with water gently, and then immersed for 30 to 60 minutes in a container containing a required volume of water (a tap water or purified water) to which one pack of the kit of the present invention has been added. In the early period of the immersion, the stains adhering to the contact lens are removed by the oxidizing agent; then, the reducing agent dissolves slowly and completes treatment for making the residual oxidizing agent nontoxic. When the reducing agent takes a form of tablets, the completion timing of the treatment of the residual oxidizing agent by the reducing agent for making the residual oxidizing agent nontoxic can be clearly confirmed visually by the disappearance of tablets in treating solution. When the treatment is over, the lens is gently washed with water and then worn or stored in a special preservative solution. If the lens is worn directly after the treatment with the kit of the present invention without water washing, it is safe because there is no damage to eyes.

Repeated cleaning of a contact lens with the kit of the present invention has no effect on the shape, color tone, etc. of the lens. Accordingly, the kit of the present invention is very safe also from this aspect.

The present invention will be explained in further detail by way of Examples.

EXAMPLE 1

| Powder composition | |
|---|---|
| Chlorinated Lime (compound capable of releasing available chlorine) | 0.035 g |
| Lactose (filler) | 0.30 g |
| Tablet composition | |
| Citric acid (reducing agent) | 0.06 g |
| Sodium citrate (pH-adjusting agent and reducing agent) | 0.12 g |
| Sodium bicarbonate (foaming agent and pH-adjusting agent) | 0.10 g |
| Magnesium stearate (lubricant) | 0.0014 g |
| Carboxymethylethylcellulose (coating agent for tablets) | 0.02 g |

Powders having the above composition and tablets coated with a coating agent, having the above composition were prepared according to ordinary methods. They were packed in a three sides-sealed aluminum package. The package was opened and the contents was placed in 10 ml of a tap water. Immediately, an oxygen-permeable hard contact lens (Hoya Hard/OP) having stains as a result of actual wearing was immersed in the solution. In about 15 minutes after the powder had dissolved, the tablets began to dissolve with foaming. In about 60 minutes, the tablets completed dissolution. The lens was taken out from the solution and washed with a tap water gently, then its surface was observed using a stereoscopic microscope of 20 magnification manufactured by Neitz. The stains had been removed completely. The solution after treatment had a pH of 7.1 and an osmotic pressure of 350 mOsm.

EXAMPLE 2

| Powder composition | |
|---|---|
| Chlorinated Lime (compound capable of releasing available chlorine) | 0.045 g |
| Dextrose (filler) | 0.20 g |
| Tablet composition | |
| Citric acid (reducing agent) | 0.08 g |
| Sodium citrate (reducing agent and pH-adjusting agent) | 0.15 g |
| Potassium bicarbonate (forming agent and pH-adjusting agent) | 0.10 g |
| Magnesium stearate (lubricant) | 0.0007 g |
| Polyethylene glycol 6000 (lubricant) | 0.01 g |
| Carboxymethylethylcellulose (coating agent for tablets) | 0.015 g |

Powders having the above composition and tablets coated with a coating agent, having the above composition were prepared according to ordinary methods. They were packed in a stick-shaped aluminum package. The package was opened and the contents was placed in 10 ml of purified water. Immediately, a soft contact lens (Hoya Soft) having stains as a result of actual wearing was immersed in the solvent. In about 5 minutes after the powder had dissolved, the tablets began to dissolve with foaming. In about 30 minutes, the tablets completed dissolution. The lens was taken out of the solution and washed with purified water gently. After the water on the lens surface had been wiped off, the lens surface was observed using a stereoscopic microscope of 20 magnification manufactured by Neitz. The stains had been removed completely. The solution after treatment had a pH of 7.3 and an osmotic pressure of 310 mOsm.

EXAMPLE 3

| Powder composition | |
|---|---|
| Chloramine T (compound capable of releasing available chlorine) | 0.10 g |
| Lactose (filler) | 0.10 g |
| Tablet composition | |
| Ascorbic acid (reducing agent) | 0.01 g |
| Sodium citrate (reducing agent and pH-adjusting agent) | 0.10 g |
| Sodium bicarbonate (foaming agent and pH-adjusting agent) | 0.12 g |
| Talc (lubricant) | 0.003 g |
| Methacrylic acid-ethyl acrylate copolymer (coating agent for tablets) | 0.03 g |

Powders having the above composition and tablets coated with a coating agent, having the above composition were prepared according to ordinary methods. They were packed in a three sides-sealed aluminum package. The package was opened and the contents was placed in 10 ml of purified water. Immediately, a soft contact lens (Hoya Soft T40) which was made cloudy as a result of artificial staining was immersed in the solution. The lens was taken out of the solution after the tablets had completed dissolution, and washed with water gently. The water on the lens surface was wiped off and the lens surface was observed. The cloudiness had been removed completely. An oxygen-permeable hard contact lens (Hoya Hard/OP) which was made cloudy as a result of artificial staining was subjected to the same procedure. The cloudiness had been removed completely.

The artificial staining was conducted as follows.

1.0 g of lysozyme, 1.0 g of alubumin and 0.9 g of sodium chloride were dissolved in purified water and the total volume was made 100 ml. This solution was used as a staining solution. A lens was immersed in this staining solution. The system was heated at 80° C. for 2 hours. This procedure was repeated five times, whereby the lens was allowed to have stains.

EXAMPLE 4

Contact lenses (Hoya Soft, Hoya Soft/T40, Hoya Hard and Hoya Hard/OP) were subjected to repeated treatments 8sing the kits of Examples 1 to 3, whereby the effects of these treatments on the shapes of said contact lenses were examined. The results are shown in Table 1. Further, a hard contact lens (Hoya Hard), an oxygen permeable hard contact lens (Menicon $O_2$ ®, manufactured by Toyo Contact Lens Co.) and a highly oxygen-permeable hard contact lens (Menicon EX ®, manufactured by Toyo Contact Lens Co.) were subjected to the same repeated treatments, whereby the effects of the treatments on the discoloration of these lenses were examined. The results are shown in Tables 1 and 2.

TABLE 1

| | | Soft contact lens | | | | | | Oxygen-permeable hard contact lens | |
|---|---|---|---|---|---|---|---|---|---|
| | | Hoya soft | | Hoya Soft T40 | | Hoya Hard | | Hoya Hard OP | |
| | | Before treatment | After 100 times treatment | Before treatment | After 100 times treatment | Before treatment | After 100 times treatment | Before treatment | After 100 times treatment |
| Kit of Example 1 | BC*[1] | 8.4 | 8.4 | 8.1 | 8.1 | 7.60 | 7.60 | 7.40 | 7.40 |
| | Power*[2] | −2.50 | −2.25 | −3.00 | −2.75 | −8.00 | −8.00 | +8.00 | +8.00 |
| | Size*[3] | 13.3 | 13.2 | 13.3 | 13.1 | 8.8 | 8.8 | 8.5 | 8.5 |
| | Thickness*[4] | 0.20 | 0.19 | 0.06 | 0.05 | 0.08 | 0.08 | 0.42 | 0.42 |
| Kit of Example 2 | BC | 8.1 | 8.1 | 8.7 | 8.7 | 8.00 | 8.00 | 7.20 | 7.20 |
| | Power | −3.00 | −3.00 | −8.00 | −8.00 | −3.00 | −3.00 | −15.00 | −15.00 |
| | Size | 13.3 | 13.3 | 13.3 | 13.3 | 8.8 | 8.8 | 8.5 | 8.5 |
| | Thickness | 0.16 | 0.16 | 0.06 | 0.06 | 0.08 | 0.08 | 0.08 | 0.08 |
| Kit of Example 3 | BC | 8.7 | 8.7 | 8.4 | 8.4 | 7.20 | 7.20 | 8.00 | 8.00 |
| | Power | −4.50 | −4.25 | +3.00 | +3.00 | +3.00 | +3.00 | −3.00 | −3.00 |
| | Size | 13.3 | 13.4 | 13.3 | 13.4 | 8.8 | 8.8 | 8.5 | 8.5 |
| | Thickness | 0.16 | 0.17 | 0.19 | 0.20 | 0.29 | 0.29 | 0.13 | 0.13 |

Note
*[1]BC — Base curve of lens (curvature at the back side)
*[2]Power — Refraction power of lens at the apex
*[3]Size — Diameter of lens
*[4]Thickness — Thickness of lens

TABLE 2

| | Color tone after 100 times treatment with: | | |
|---|---|---|---|
| | Example 1 kit | Example 2 kit | Example 3 kit |
| Hoya Hard (Light green) | No change of color tone (Light green) | No change of color tone (Light green) | No change of color tone (Light green) |
| Menicon $O_2$ ® (Light gray) | No change of color tone (Light gray) | No change of color tone (Light gray) | No change of color tone (Light gray) |

TABLE 2-continued

| | Color tone after 100 times treatment with: | | |
|---|---|---|---|
| | Example 1 kit | Example 2 kit | Example 3 kit |
| Menicon EX ® (Light blue) | No change of color tone (Light blue) | No change of color tone (Light blue) | No change of color tone (Light blue) |

As obvious from Tables 1 and 2, in repeated cleaning of contact lenses using the kits of Examples 1 to 3, neither parameter changes not discoloration occurred in any lenses. Thus, it was confirmed that the kit of the present invention has no effect on the shape, etc. of contact lens.

Next, the amount of available chlorine remaining in the solution after treatment when the kits of Examples 1 to 3 were used was measured in accordance with the color reaction by o-toluidine hydrochloride. In all the cases of Examples 1 to 3, the solutions after treatment gave no color development indicating presence of residual available chlorine. In contrast, all of the treating solutions containing only powders (the oxidizing agent) and containing no tablets (the reducing agent) gave distinct color development. The solution after treatment when the kits of the present invention were used, were dropped in eyes, but there was neither stimulus nor damage to the cornea.

Thus, it was confirmed that the treating solution using the kit of the present invention gives no damage to eyes and is safe.

What is claimed:

1. A kit for contact lens cleaning, comprising an oxidizing agent for removing stains adhering to contact lenses selected from the group consisting of chlorinated lime, chloramine T, chloramine B and halazone and a reducing agent for making nontoxic the oxidizing agent still remaining after stain removal selected from the group consisting of citric acid, malic acid, tartaric acid and salts thereof, wherein the oxidizing agent and the reducing agent are each in such form that they do not substantially react with each other in the kit and that, when they are placed in water substantially simultaneously, the major portion of the oxidizing agent dissolves in the water more rapidly than the major portion of the reducing agent, the oxidizing agent being in the form of powder or granules and the reducing agent being in the form of tablets or in the form of powder or granules contained within a bag or having a coating thereon.

2. A kit according to claim 1, wherein the tablets are coated with a coating agent.

3. A kit according to claim 1, wherein the tablets are effervescent tablets.

4. A kit according to claim 1, wherein the oxidizing agent and the reducing agent are contained in a package.

5. A kit according to claim 4, wherein the package is a three sides-sealed aluminum package or a stick-shaped aluminum package.

6. A method for cleaning contact lenses wherein an oxidizing agent selected from the group consisting of chlorinated lime, chloramine T, chloramine B and halazone is used for removing stains adhering to said lenses and a reducing agent selected from the group consisting of citric acid, malic acid, tartaric acid and salts thereof is used to render non-toxic the residual oxidizing agent after stain removal, said oxidizing agent being in the form of a powder or granules and said reducing agent being in the form of tablets or in the form of powder or granules contained within a bag or having a coating thereon, which comprises introducing said oxidizing agent and reducing agent substantially simultaneously into water, dissolving the major portion of the oxidizing agent in the water more rapidly than the major portion of the reducing agent, immediately cleaning contact lenses in the water with the dissolved oxidizing agent, and thereafter reducing the residual oxidizing agent with the reducing agent so as to render said lenses nontoxic.

7. A method according to claim 6, wherein the tablets are effervescent tablets.

8. A method according to claim 6, wherein the treating solution after the completion of cleaning is isotonic with and has the same pH as the human lacrima.

9. A method according to claim 6, wherein the concentration of the oxidizing agent after dissolution in water is 5.0 to 0.005% by w/v.

10. A method according to claim 6, wherein the concentration of the reducing agent after dissolution in water is 10.0 to 0.05% by w/v.

* * * * *